US009727998B2

(12) United States Patent
Graumann

(10) Patent No.: US 9,727,998 B2
(45) Date of Patent: Aug. 8, 2017

(54) APPARATUS AND METHOD FOR VIRTUAL SPATIAL RECONSTRUCTION OF A SURGICAL TOOL

(71) Applicant: SIEMENS HEALTHCARE GMBH, Erlangen (DE)

(72) Inventor: Rainer Graumann, Hoechstadt (DE)

(73) Assignee: Siemens Healthcare GmbH, Erlangen (DE)

( * ) Notice: Subject to any disclaimer, the term of this patent is extended or adjusted under 35 U.S.C. 154(b) by 34 days.

(21) Appl. No.: 13/875,403

(22) Filed: May 2, 2013

(65) Prior Publication Data

US 2013/0293535 A1 Nov. 7, 2013

(30) Foreign Application Priority Data

May 2, 2012 (DE) .................. 10 2012 207 261

(51) Int. Cl.
*G06T 15/00* (2011.01)
*G06T 7/73* (2017.01)
*A61B 90/00* (2016.01)

(52) U.S. Cl.
CPC ................ *G06T 15/00* (2013.01); *G06T 7/73* (2017.01); *A61B 2090/3966* (2016.02); *G06T 2207/10116* (2013.01); *G06T 2207/20068* (2013.01); *G06T 2207/30021* (2013.01)

(58) Field of Classification Search
None
See application file for complete search history.

(56) References Cited

U.S. PATENT DOCUMENTS

| | | | |
|---|---|---|---|
| 6,203,485 B1* | 3/2001 | Urick .................. | A61N 5/1002 600/3 |
| 7,840,254 B2* | 11/2010 | Glossop ................ | A61B 19/52 600/424 |
| 2006/0013355 A1* | 1/2006 | Heismann ............. | A61B 6/032 378/4 |
| 2009/0054762 A1 | 2/2009 | Burgkart | |
| 2011/0135183 A1 | 6/2011 | Bismuth et al. | |
| 2012/0082360 A1 | 4/2012 | Florent | |
| 2013/0158512 A1* | 6/2013 | Gutierrez et al. ............ 604/510 | |
| 2013/0267829 A1* | 10/2013 | Ojha et al. .................... 600/411 | |
| 2013/0308843 A1* | 11/2013 | Tank ...................... | A61C 19/04 382/128 |

FOREIGN PATENT DOCUMENTS

| | | |
|---|---|---|
| DE | 102007008521 A1 | 8/2007 |
| DE | 102010041564 A1 | 3/2012 |
| GB | 2473326 A | 3/2011 |
| WO | 2010150145 A1 | 12/2010 |

* cited by examiner

*Primary Examiner* — Jwalant Amin
(74) *Attorney, Agent, or Firm* — Laurence Greenberg; Werner Stemer; Ralph Locher

(57) ABSTRACT

An apparatus and a method determine a virtual spatial reconstruction of a surgical tool imaged in a 2D x-ray image. A reconstruction module segments a 2D image of at least one element of the surgical tool in the 2D x-ray image and a spatial reconstruction of the at least one element is implemented after the spatial configuration of the 2D image of the at least one element is determined.

13 Claims, 4 Drawing Sheets

APPARATUS AND METHOD FOR VIRTUAL SPATIAL RECONSTRUCTION OF A SURGICAL TOOL

CROSS-REFERENCE TO RELATED APPLICATION

This application claims the priority, under 35 U.S.C. §119, of German application DE 10 2012 207 261.6, filed May 2, 2012; the prior application is herewith incorporated by reference in its entirety.

BACKGROUND OF THE INVENTION

Field of the Invention

The present invention lies in the field of medical technology, and relates in particular to an approach involving localizing surgical tools, in respect of their alignment and position in a medical intervention.

A Kirschner wire, also known as K-wire, is used for instance in surgical interventions on the patient. The K-wire is in this way used very frequently for temporary fixing purposes or as a guide wire for subsequent fixing activities. To this end, the obtaining of navigation assistance for planned work steps is helpful to the work of a surgeon. Therefore the position and orientation of medical tools must be determined for instance. In order to determine the position of the K-wire, star-shaped orientation elements can be attached thereto and identified in the space by means of an x-ray and/or optical navigation system. Upon evaluation of the x-ray images with the star-shaped orientation elements, a punctiform orientation of the K-wire outside of an intervention area is possible.

SUMMARY OF THE INVENTION

It is accordingly an object of the invention to provide an apparatus and a method for virtual spatial reconstruction of a surgical tool which overcome the above-mentioned disadvantages of the prior art methods and devices of this general type, such that its position in the space can be determined.

The apparatus and method for the virtual spatial reconstruction of a surgical tool imaged in a 2D x-ray image is such that the surgical tool contains at least one first element with a first x-ray attenuation coefficient and that a reconstruction model is provided, as a result of which the 2D image of the at least one element in the x-ray image is segmented and a spatial reconstruction of the at least one element is implemented after determining the spatial arrangement of the 2D image of the at least one element.

The surgical tool, in particular a K-wire, is embodied according to the invention such that this has at least one elongated cylindrical sub component with an x-ray attenuation coefficient.

The invention is advantageous in that a spatial orientation of a K-wire can be derived from a 2D x-ray recording.

The invention is advantageous in that a spatial assignment can be determined between a K-wire and an implant.

The invention is advantageous in that a 3D scale can be determined by use of the K-wire.

The invention is advantageous in that a 3D reconstruction of deformed K-wires is possible.

The invention is advantageous in that a stability forming the K-wire is not negatively affected.

The invention is advantageous in that this can be used in minimally invasive operations.

Other features which are considered as characteristic for the invention are set forth in the appended claims.

Although the invention is illustrated and described herein as embodied in an apparatus and a method for virtual spatial reconstruction of a surgical tool, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

The apparatus described below and the associated method enable a spatial reconstruction of a surgical tool imaged in a 2D x-ray image.

Figure 1:
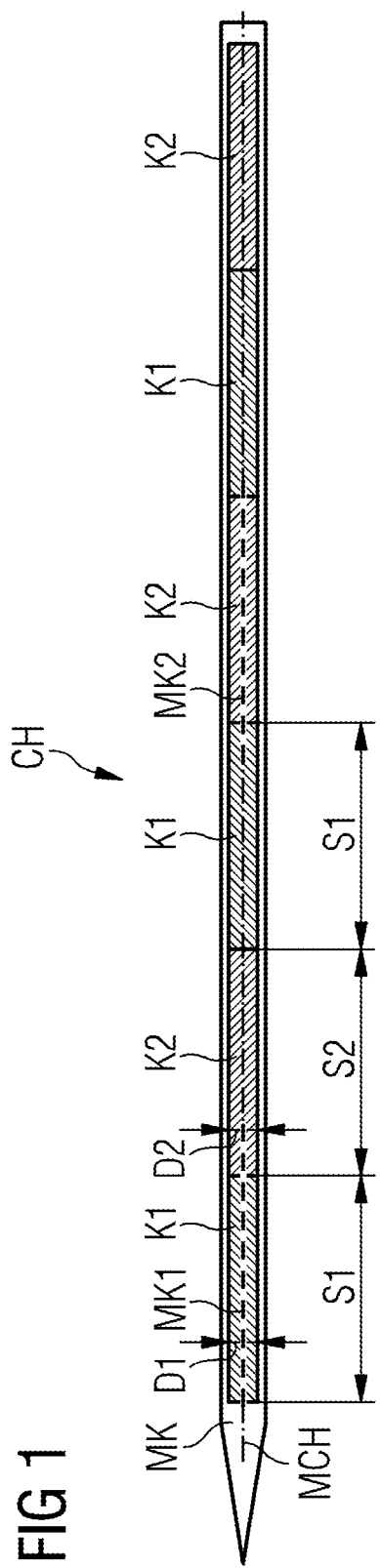
FIG. 1 is a diagrammatic, side view of a surgical tool according to invention.

Referring now to the figures of the drawing in detail and first, particularly, to FIG. 1 thereof, there is shown an embodiment of a surgical tool CH. In this schematic representation, the surgical tool CH is formed in an embodiment of a K-wire. The K-wire may be embodied with different lengths and with different diameters. The K-wire CH imaged here has at least one element K1, K2, MK. In FIG. 1, an exemplary embodiment is shown with a plurality of elements. The elements can be first and second elements K1, K2 arranged one behind the other and a further element in the form of a cladding encasing the first and second elements. The first and second elements, subsequently referred to as first and second core K1, K2, may have different diameters and different lengths. The data relating to the individual cores of the K-wires is available to a computing unit RE (not explicitly shown) in accessible tables or can be acquired by coding assigned to the K-wire. The coding can be added to the relevant core, e.g. by perforation, or determined in a calibration step prior to use. When aligned, the first and second cores K1, K2 produce the core of the K-wire. The first core K1 has a first material with a first x-ray attenuation coefficient R1 and the second core K2 has a second material with a second x-ray attenuation coefficient R2. The first and second cores K1 and K2 aligned adjacent to one another on a central axis MCH are encased with a cylindrically embodied sleeve and/or cladding MK for instance. The sleeve and/or cladding MK is formed from a third homogenous material having an x-ray attenuation coefficient R3. The third x-ray attenuation coefficient R3 of the cladding MK can correspond to that of the first or second x-ray attenuation coefficient R1, R2. The first and second cores K1, K2 embodied cylindrically for instance each contain a defined first and second length S1, S2 and a defined first and second diameter D1, D2. The first and second cores can be arranged repeatedly so as to lie directly one behind the other on the central axis MCH or at a defined distance within the cladding MK. The central axes MK1, MK2 of the first and second cores are disposed in a defined manner in respect of the central axis MCH of the K-wire. In the exemplary embodiment shown, the central axes MK1, MK2 of the first and second cores K1, K2 are disposed on the central axis MCH of the K-wire. The different cores K1, K2 and possibly also the cladding MK of the surgical tool CH are imaged in an x-ray image RB with distinctive gray-scale values on account of their different x-ray attenuation coefficient.

Figure 2:
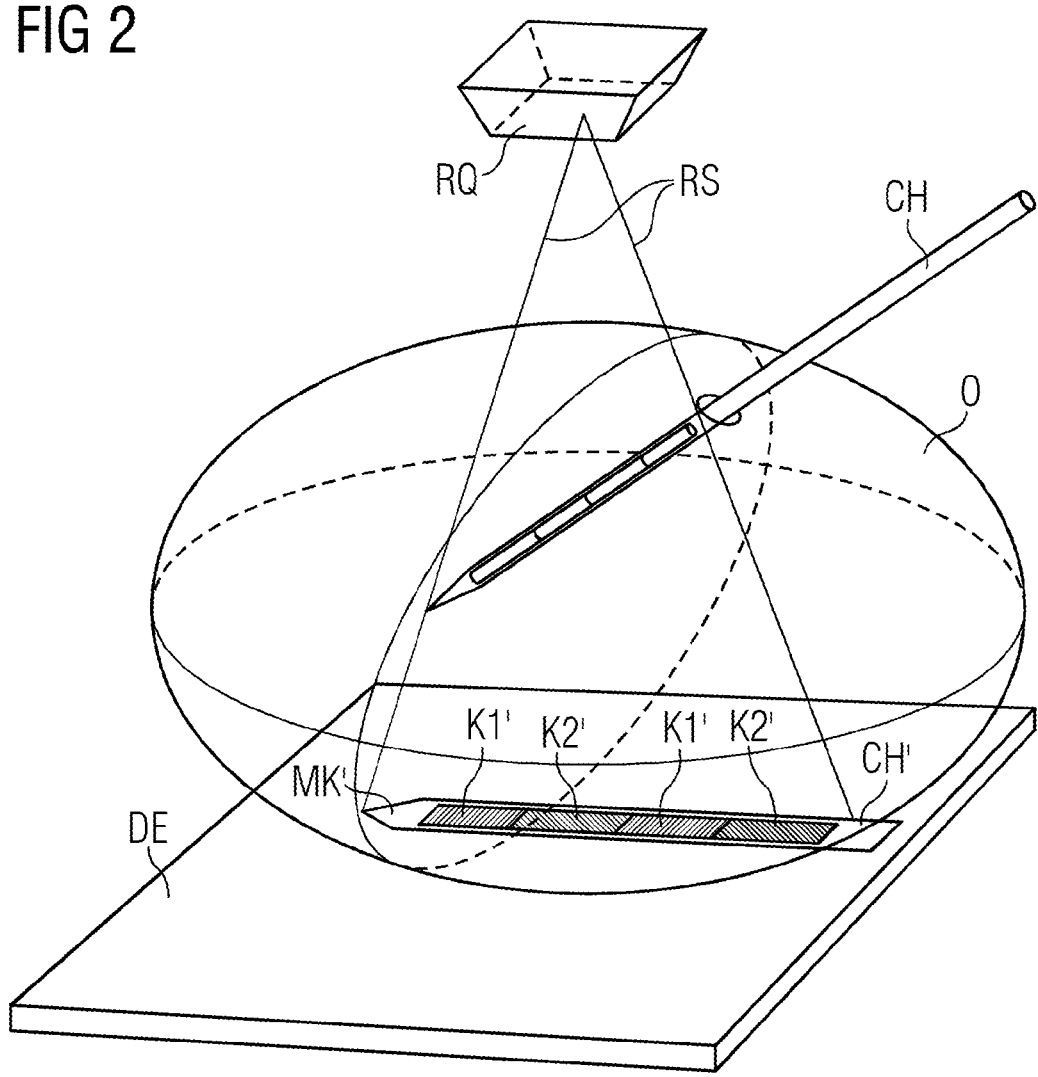
FIG. 2 is a schematic representation showing the surgical tool in use in an X-ray system.

FIG. 2 reproduces a schematic representation of an x-ray system. An object O is placed on a detector DE. A K-wire is introduced into the object O. With an x-ray recording, the x-rays RS originating from the x-ray source RQ of the x-ray system penetrate the object O and the K-wire. The digital x-ray image RB which can be read out from the detector DE has distinctive gray-scale value images of the cores K1', K2' and of the cladding MK' of the K-wire CH and further gray-scale values of the object O (not shown explicitly here).

Figure 3:
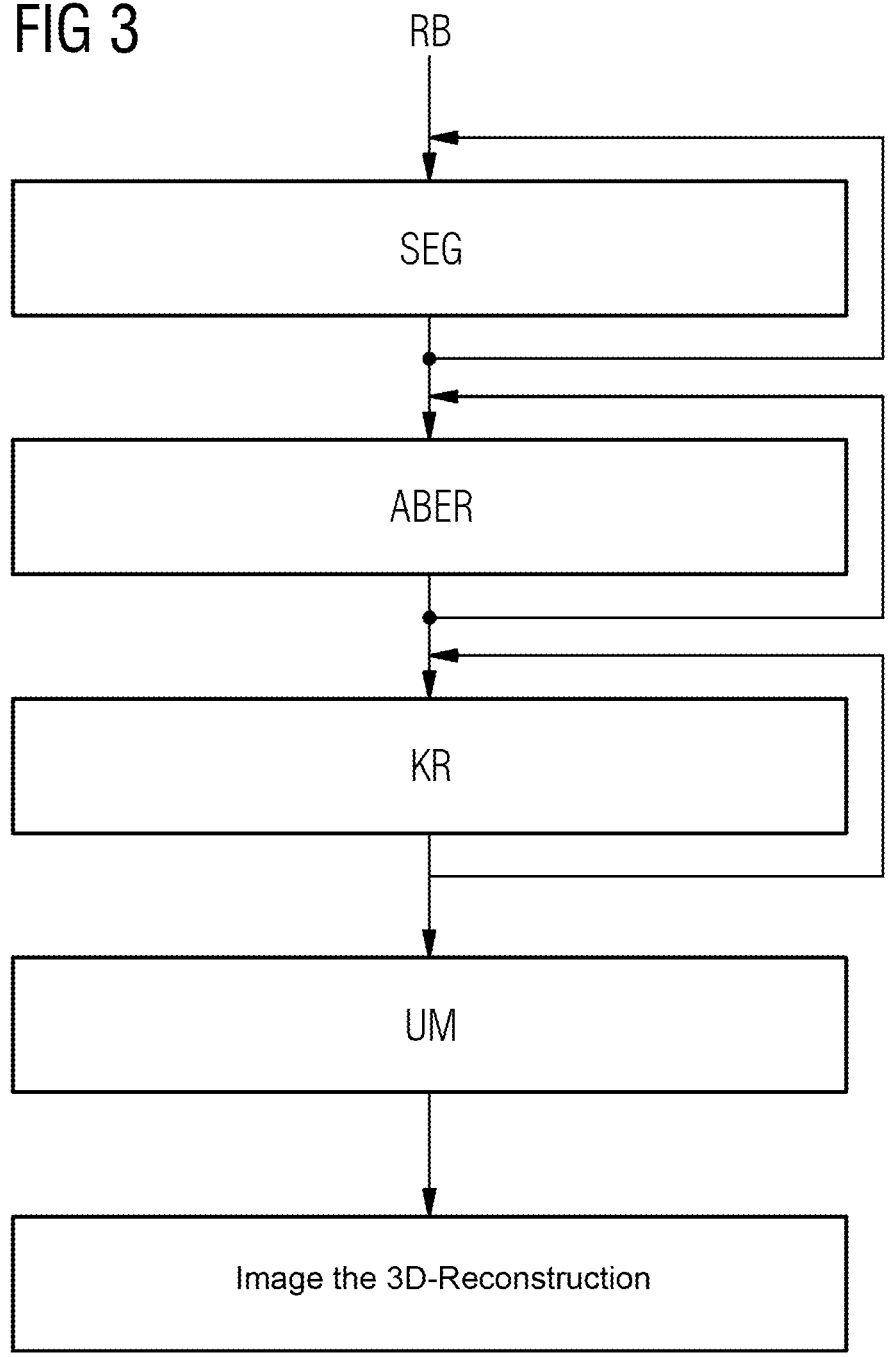
FIG. 3 is a flow chart for explaining a method of use of the surgical tool.

FIG. 3 shows a flow chart of a reconstruction algorithm within a reconstruction module RA for the virtual reproduction of the K-wire CH with the aid of its gray-scale value images in a digital x-ray image RB. The method steps to be implemented are implemented with a segmentation module SEG for segmenting the first and second cores K1', K2" imaged in the x-ray image RB, and the cladding MK', a distance determination module ABER for calculating distances ABn from cores K1, K2 to be imaged or the cladding MK from the detector surface DE, a core reconstruction module KR for spatial reconstruction of the cores K1", K2" and a cladding module UM for the spatial reconstruction of the cladding MK" about the reproduction of the cores K1", K2". The computing processes of the individual method steps, in which cited modules SEG, ABER, KR and UM are described as above, are implemented in a computing unit RE provided for the respective medical unit. The calculated spatial reconstruction of the K-wire is imaged on a monitor arranged adjacent to the medical device.

Figure 4:
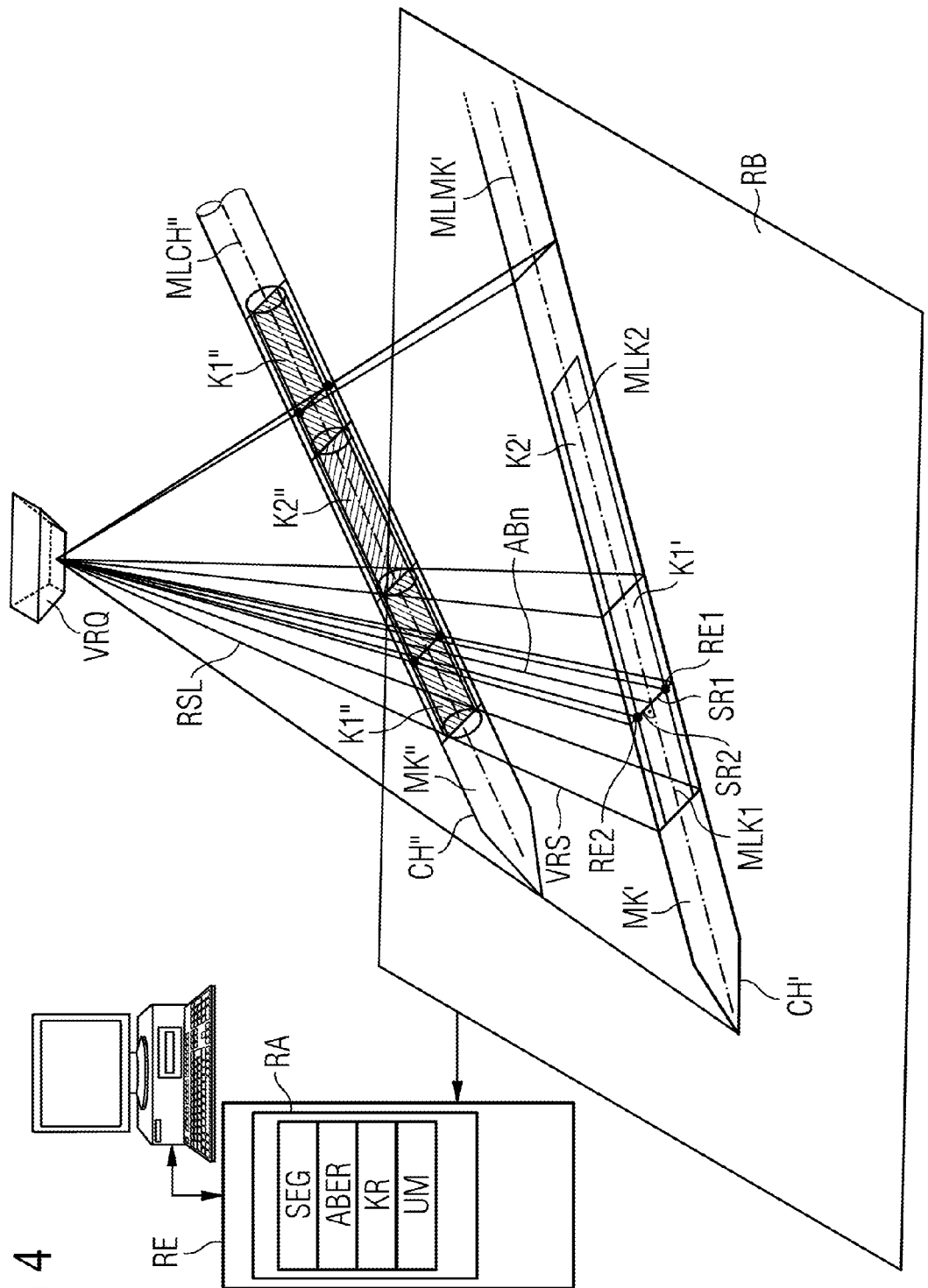
FIG. 4 is a schematic representation showing the surgical tool in use in the X-ray system.

FIG. 4 shows a sketch of construction lines for a virtual 3D reconstruction of the K-wire CH with the aid of gray-scale value images of the K-wire CH' in a digital x-ray image RB. The K-wire CH' reproduced in the x-ray image RB and the 3D reconstruction of the K-wire CH" are imaged. In a first step, the planar images of the first and second cores K1', K2' and of the cladding MK' in the digital x-ray image RB are segmented by the computing operations assigned to the segmentation module. In order to determine the spatial arrangement of the cores Kn" to be reproduced, a plurality of partial distances ABn from the detector surface DE or the digital x-ray image RB are calculated in a second step in respect of a selected 2D image of a core Kn' or a cladding MK'. The laws of radiation geometry are used in order to calculate the distances ABn. The distance is determined by the theorem on intersecting lines with the aid of the respective diameter Dn of a core Kn, the width of the 2D image of the respective core Kn in the x-ray image and the distance between the x-ray source RQ and detector DE. The coordinates of the x-ray beam entry points REn into the detector plane must be determined in order to determine the distance between the x-ray source RQ and the detector DE. The x-ray beam entry points REn form the end points of the x-rays RS which have their starting point in the x-ray source RQ. The x-ray beam entry points REn are disposed directly on the edge of the respective 2D image of the cores KN' or the cladding MK'. In order to determine the x-ray beam entry points REn, perpendicular lines SRn are established on the center lines MLKn', MLMK' of the individually selected 2D images of the cores Kn' and the cladding MK'. A first and second perpendicular line SR1, SR2 in respect of both sides of the respective center line MLKn' are established based on a x, y coordinate on the center line MLKn', MLMK' of the imaged core Kn'. The coordinates of the x-ray beam entry point REn are provided by the coordinates of the edge points of the selected surface of the core Kn' or cladding MK'. The coordinates of the starting point for the x-rays of the x-ray source RQ are known. The x-ray length RSL, the length of the first and second perpendicular line SR1, SR2 and the diameter Dn of the respectively observed core Kn or cladding MK are thus known. The theorem on intersecting lines allows the distance of the imaged core Kn from the detector surface and/or from the x-ray image RB to be determined. In addition to the range between the x-ray source RQ and the detector DE, the parameter values for exposure time and diaphragm setting are also available here for the current evaluation of the x-ray image RB in a computing unit (not shown here in further detail). Upon conclusion of the computing process of the second step, a 2D image of the core Kn' projected into the space is available. This procedure is repeated with the further selected 2D images. These operations are implemented by the distance determination module ABER.

In a third step, the computing operations are implemented for the reconstruction of the cores in the core reconstruction module KR. With computing processors of the core reconstruction algorithm arranged in the core reconstruction module KR, the data of the respective core Kn and cladding MK is transferred to the length and alignment of the 2D image of the core Kn" projected into the space. The computing processes of the core reconstruction algorithm are implemented for each 2D image of a core K' projected into the space. Upon conclusion of the computing processes, virtual 3D reproductions K" of the selected 2D images of the cores K' exist.

In a subsequent fourth step, the individual virtual reproductions of the cores Kn are surrounded by a cladding MK". This virtual cladding MK" is implemented using computing operations of an encasing algorithms assigned to the encasing module UM. The data relating hereto is present for the encasing algorithm.

Upon conclusion of the subsequent processing step, a 3D data record of the virtual reproduction of the K-wire and/or of the surgical tool exists.

If a 3D data volume record has been created prior to entry into the treatment room by the patient, the virtual reproduction of the K-wire CH can be superimposed herein with the aid of the known coordinates of the 3D data volume set. With the aid of the two data records, target coordinates and an associated alignment of the K-wire can be determined.

The spatial reconstruction of the entire K-wire can be mapped for instance to form a similarly superimposed or reconstructed implant in a data volume record.

LIST OF REFERENCE CHARACTERS

CH surgical tool, K-wire
MK cladding/sleeve of the K-wire
R1 first x-ray attenuation coefficient
R2 second x-ray attenuation coefficient
R3 third x-ray attenuation coefficient
S1 first length S2 second length
D1 first diameter
D2 second diameter
MK' x-ray image of the K-wire cladding
MK" virtual reproduction of the K-wire cladding
K1 first core/first element
K1' x-ray image of the first core, 2D image of the first core
K1" virtual reproduction of the first core
K2 second core/second element
K2' x-ray image of the second core, 2D image of the second core
K2" virtual reproduction of the second core
MCH central axis of the K-wire
MK1 central axis of the first core
MK2 central axis of the second core
RE1, . . . , REn x-ray beam entry points
O object
VRQ virtual x-ray source
RS x-rays
CH' x-ray image of the surgical tool
CH" virtual reconstruction of the surgical tool
VRS virtual x-ray beam
ABn partial distance
RB x-ray image, digital x-ray image
RQ x-ray source
DE detector
AB partial distance
MLMK' center line of the imaged cladding
MLKn' center line of the imaged core
SRn perpendicular line
RA reconstruction module
SEG segmentation module
ABER distance determination module
KR core reconstruction module
UM encasing module

The invention claimed is:

1. An apparatus for virtual spatial reconstruction of a surgical tool, the apparatus comprising:
a computing unit programmed to process a 2D x-ray image of a surgical tool formed as a Kirschner wire with a cladding encasing a plurality of elements including a first core extending along an axis and a second core extending along the axis, the first and second cores disposed one behind the other, wherein the 2D x-ray image of the surgical tool has distinctive gray-scale value images of the plurality of elements resulting from different x-ray attenuation coefficients of the plurality of elements;
said computing unit programmed for segmenting a 2D image of the plurality of elements in the 2D x-ray image, determining a spatial configuration of the plurality of elements by calculating a plurality of partial distances from a reference plane to the plurality of elements, and implementing a spatial reconstruction of the plurality of elements after determining the spatial configuration.

2. The apparatus according to claim 1, wherein said computing unit is programmed for determining coordinates of x-ray beam entry points at an edge of the 2D image extracted from the 2D x-ray image of the plurality of elements of the surgical tool, and a spatial position of the 2D image of the plurality of elements is calculated based on coordinates of the x-ray beam entry points.

3. The apparatus according to claim 1, wherein said computing unit is programmed for a virtual reconstruction of the plurality of elements on a basis of its construction data and a spatial configuration of the 2D image of the plurality of elements imaged in the 2D x-ray image.

4. The apparatus according to claim 1, wherein said computing unit is programmed for virtually encasing a plurality of virtually reconstructed elements with an aid of present data of cladding of the surgical tool.

5. The apparatus according to claim 1, wherein the first and second cores and the cladding form a cylindrical homogenous structure.

6. The apparatus according to claim 1, wherein the first and second cores each have a defined distance relative to one another.

7. The apparatus according to claim 1, wherein the 2D x-ray image includes an image of the plurality of elements of the surgical tool, and second core has an x-ray attenuation coefficient that is different than the x-ray attenuation coefficient of the first core.

8. The apparatus according to claim 1, wherein the reference plane is a surface of a detector or the 2D x-ray image.

9. A method for a virtual spatial reconstruction of a surgical tool, which comprises the steps of:
providing a computing unit with a 2D x-ray image of a surgical tool formed as a Kirschner wire with a cladding encasing a plurality of elements including a first core extending along an axis and a second core extending along the axis the first and second cores disposed one behind the other, wherein 2D x-ray image of the surgical tool has distinctive gray-scale value images of the plurality of elements resulting from different x-ray attenuation coefficients of the plurality of elements;
in the computing unit, segmenting a 2D image of the plurality of elements in the 2D x-ray image;
in the computing unit, determining a spatial configuration of the plurality of elements by calculating a plurality of partial distances from a reference plane to the plurality of elements; and
in the computing unit, implementing a spatial reconstruction of the plurality of elements following determination of the spatial arrangement.

10. The method according to claim 9, which further comprises:
in the computing unit, determining coordinates of x-ray beam entry points at an edge of 2D images extracted from the 2D x-ray image by the plurality of elements of the surgical tool; and
in the computing unit, calculating a spatial position of an extracted 2D image of the plurality of elements based on the coordinates of the x-ray beam entry points.

11. The method according to claim 9, which further comprises: in the computing unit, implementing a virtual spatial reconstruction of the plurality of elements on a basis of its construction data and the spatial arrangement of the 2D image of the plurality of elements.

12. The method according to claim 9, wherein the 2D x-ray image includes an image of the plurality of elements of the surgical tool, and second core has an x-ray attenuation coefficient that is different than the x-ray attenuation coefficient of the first core.

13. The method according to claim 9 wherein the reference plane is a surface of a detector or the 2D x-ray image.

* * * * *